United States Patent
Guo et al.

(10) Patent No.: US 8,349,727 B2
(45) Date of Patent: Jan. 8, 2013

(54) INTEGRATED METHOD FOR HIGH-DENSITY INTERCONNECTION OF ELECTRONIC COMPONENTS THROUGH STRETCHABLE INTERCONNECTS

(76) Inventors: Liang Guo, Cambridge, MA (US); Stephen P. DeWeerth, Mendota, IL (US)

( * ) Notice: Subject to any disclaimer, the term of this patent is extended or adjusted under 35 U.S.C. 154(b) by 10 days.

(21) Appl. No.: 13/083,111

(22) Filed: Apr. 8, 2011

(65) Prior Publication Data
US 2011/0254171 A1    Oct. 20, 2011

Related U.S. Application Data

(60) Provisional application No. 61/322,110, filed on Apr. 8, 2010.

(51) Int. Cl.
*H01L 21/4763* (2006.01)

(52) U.S. Cl. ........ 438/637; 438/667; 438/672; 438/675; 257/E23.011; 257/758; 257/774

(58) Field of Classification Search .......... 438/629, 438/637, 639, 640, 667, 668, 672, 675, 700, 438/701, 713, 978; 257/E23.011, 758, 773–776; 427/98.4; 216/20
See application file for complete search history.

(56) References Cited

U.S. PATENT DOCUMENTS

| | | | |
|---|---|---|---|
| 4,029,562 A * | 6/1977 | Feng et al. | 438/629 |
| 4,272,561 A * | 6/1981 | Rothman et al. | 438/570 |
| 4,599,243 A * | 7/1986 | Sachdev et al. | 216/18 |
| 4,783,695 A | 11/1988 | Eichelberger et al. | |
| 5,065,227 A | 11/1991 | Frankeny et al. | |
| 5,773,889 A * | 6/1998 | Love et al. | 257/737 |
| 6,324,429 B1 | 11/2001 | Shire et al. | |
| 6,878,643 B2 | 4/2005 | Krulevitch et al. | |
| 6,976,998 B2 | 12/2005 | Rizzo et al. | |
| 6,991,963 B2 | 1/2006 | Krulevitch et al. | |
| 7,005,179 B2 | 2/2006 | Davidson et al. | |
| 7,146,221 B2 | 12/2006 | Krulevitch et al. | |
| 7,211,103 B2 | 5/2007 | Greenberg et al. | |
| 7,326,649 B2 | 2/2008 | Rodger et al. | |
| 7,337,012 B2 | 2/2008 | Maghribi et al. | |
| 7,531,120 B2 * | 5/2009 | Van Rijn et al. | 264/299 |
| 7,706,887 B2 | 4/2010 | Tai et al. | |
| 7,774,931 B2 | 8/2010 | Tai et al. | |
| 7,820,525 B2 * | 10/2010 | Hsieh | 438/455 |
| 7,846,285 B2 | 12/2010 | Zhou et al. | |
| 2006/0029731 A1 | 2/2006 | Davidson et al. | |
| 2006/0042830 A1 | 3/2006 | Maghribi et al. | |

* cited by examiner

Primary Examiner — Chris Chu

(57) ABSTRACT

Stretchable multi-chip modules (SMCMs) are capable of withstanding large mechanical deformations and conforming to curved surfaces. These SMCMs may find their utilities in elastic consumer electronics such as elastic displays, skin-like electronic sensors, etc. In particular, stretchable neural implants provide improved performances as to cause less mechanical stress and thus fewer traumas to surrounding soft tissues. Such SMCMs usually comprise of various electronic components attached to or embedded in a polydimethylsiloxane (PDMS) substrate and wired through stretchable interconnects. However, reliably and compactly connecting the electronic components to PDMS-based stretchable interconnects is very challenging. This invention describes an integrated method for high-density interconnection of electronic components through stretchable interconnects in an SMCM. This invention has applications in high-density SMCMs, as well as high-density stretchable/conformable neural interfaces.

14 Claims, 5 Drawing Sheets

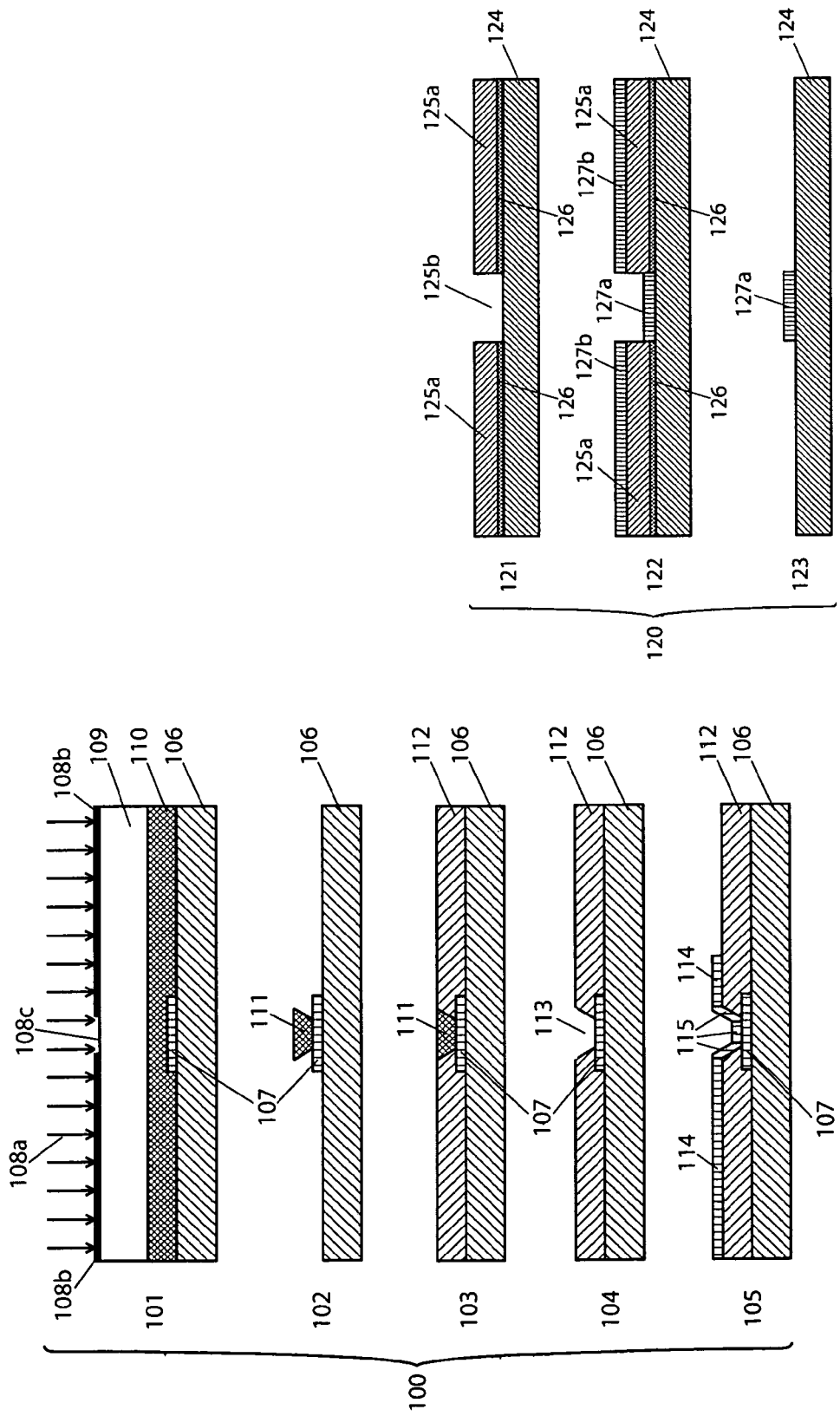

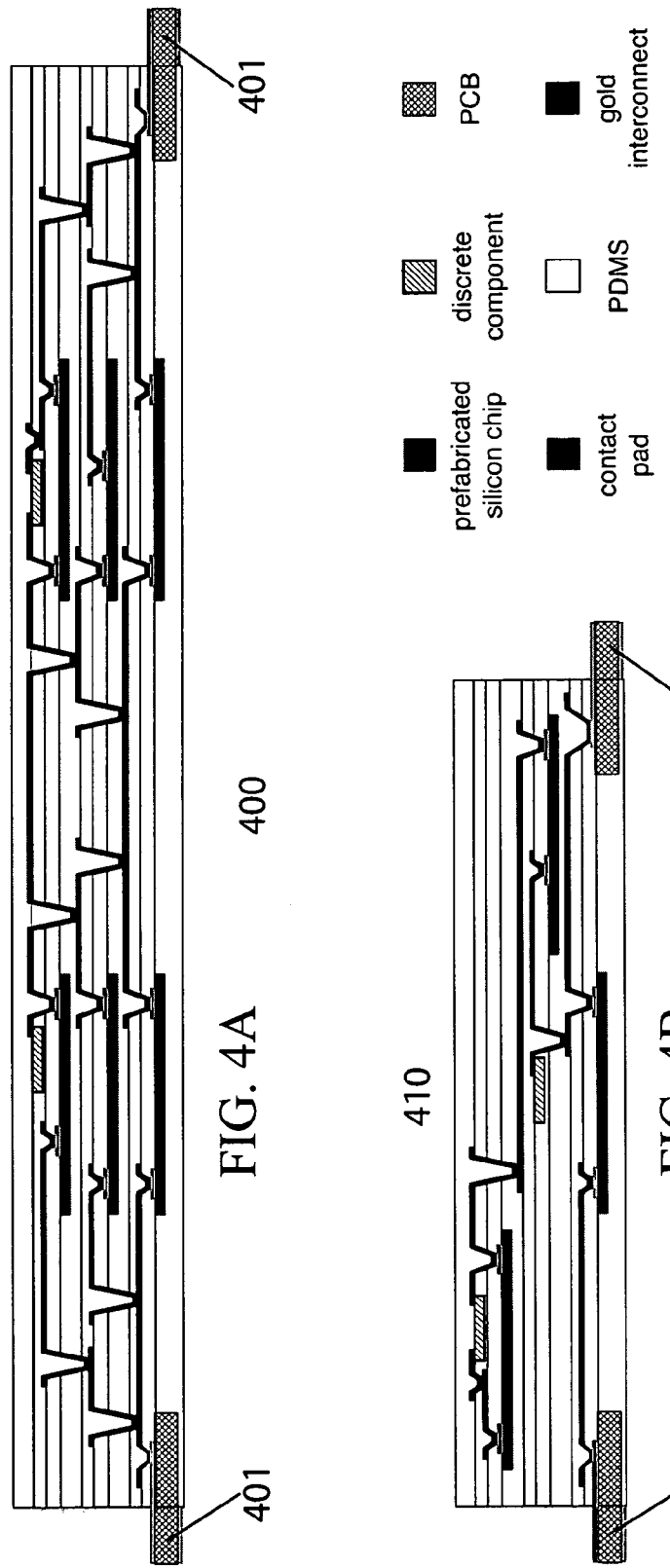

INTEGRATED METHOD FOR HIGH-DENSITY INTERCONNECTION OF ELECTRONIC COMPONENTS THROUGH STRETCHABLE INTERCONNECTS

CROSS-REFERENCE TO RELATED APPLICATIONS

This application claims the benefit of U.S. Provisional Patent Application No. 61/322,110 filed Apr. 8, 2010 and titled "Fabrication of Multilayer Wiring Interconnects on PDMS Substrate", incorporated herein by reference.

STATEMENT REGARDING FEDERALLY SPONSORED RESEARCH OR DEVELOPMENT

This invention was made with government support under Grant No. R01-EB006179 awarded by the National Institutes of Health. The government has certain rights in the invention.

REFERENCE TO SEQUENCE LISTING, A TABLE, OR A COMPUTER PROGRAM LISTING COMPACT DISC APPENDIX (Not Applicable)

BACKGROUND OF THE INVENTION

1. Field of Endeavor

The present invention relates generally to electronics interconnection and packaging, and more particularly, the invention relates to the wiring and packaging of stretchable multi-chip modules (SMCMs), including the wiring and packaging of high-density polydimethylsiloxane (PDMS)-based stretchable microelectrode arrays.

2. State of Technology

Electronics that are stretchable provide unique utilities for applications where the normal activity of the application involves large mechanical deformations or where an intimate contact to a curved surface is crucial for the proper function of the application. Example stretchable electronic systems include elastic displays, skin-like electronic sensors and stretchable/conformable neural interfaces. In one embodiment, the stretchable electronic system is constructed as a stretchable multi-chip module (SMCM), in which various electronic components including sub-circuits are attached to or embedded in a polydimethylsiloxane (PDMS) substrate as islands and wired through stretchable interconnects. The importance of reliably and compactly bonding the stretchable interconnects to the electronic components (usually rigid) becomes apparent.

In neural interfacing applications, it is revealed that neural implants made of soft materials improve performances while causing less mechanical stress and thus fewer traumas to surrounding soft tissues (Kotov, N. A., et al., Advanced Materials, 21, 1-35, 2009). Moreover, soft devices provide better flexibility and conformability to interface with curved tissue surfaces. Therefore, there is trend to fabricate neural interfaces using thinner and softer materials. In U.S. Pat. No. 7,774,931 B2, Tai et al. proposed an intraocular retinal prosthesis comprising of a parylene-based flexible retinal electrode array. The thin film electrode array can conform to the curvature of the retinal surface and deliver electrical impulses for the restoration of vision. With a Young's modulus of 4.5 GPa (Rodger, D. C., et al, Sensors and Actuators: B. Chemical, 132, 449-460, 2008), parylene is still more than five orders of magnitude stiffer than the soft retina. The biocompatibility and performance of retinal prostheses can be further improved by using electrode arrays made of even softer materials, such as PDMS whose Young's modulus of ~1 MPa (Meacham, K. W., et al., Biomedical Microdevices, 10, 259-269, 2008) is much closer to those of soft tissues. In U.S. Pat. No. 7,146,221 B2, Krulevitch et al. described the fabrication of a flexible electrode array using PDMS as the substrate and insulation material.

In a review paper by Weiland, J. D., et al., on retinal prosthesis (Weiland, J. D., et al., Annual Review of Biomedical Engineering, 7, 361-401, 2005), it is pointed out that a high-resolution retinal prosthesis would require at least 600~1000 microelectrodes in an ~3 $cm^2$ device area. It then becomes apparent that wiring such a flexible electrode array to integrated circuits (ICs) for stimulation control is technical difficult. In U.S. Pat. No. 7,326,649 B2, Rodger, D. C., et al., proposed a multilayer interconnect method for wiring the aforementioned parylene-based flexible retinal electrode array. And in U.S. Pat. No. 7,706,887 B2, Tai and Rogder extended the wiring method to incorporate pre-fabricated chips in the parylene-based retinal implant. In U.S. Pat. No. 7,211,103 B2, Greenberg, R. J., et al., described various biocompatible bonding methods for implantable electronics packaging. However, for a high-density microelectrode array made of the more advantageous material of PDMS, no effective method has been reported capable of addressing the challenge of wiring at least 600~1000 electrodes in an ~3 $cm^2$ device area for an implantable retinal electrode array. This difficulty is attributed to the viscoelastic nature of the PDMS material.

The present invention is to provide an integrated method for reliably and compactly wiring electronic components of high I/O counts in an SMCM system, including wiring PDMS-based high-density microelectrode arrays to other electronic components such as silicon chips of ICs.

BRIEF SUMMARY OF THE INVENTION

Owing to the viscoelastic nature of the PDMS material, conventional interconnection and bonding methods as used with other substrate materials (e.g., silicon, parylene, polyimide, FR4, etc.) are not applicable to PDMS-based stretchable electronics, particularly when a high I/O count electronic component, such as a PDMS-based retinal electrode array, is involved. In witnessing such challenges as to wiring electronic components in a SMCM system, the present invention developed unique microfabrication techniques for (1) patterning ultrahigh density interconnects on individual PDMS layers using an innovative SU-8 lift-off method, (2) making electrical interconnection between multiple conducting layers through purposely made inclined-vias (vertical or straight vias as widely used in other substrate systems do NOT work with PDMS substrates), and (3) bonding PDMS-based stretchable interconnects to other stiffer substrates or electronic components at high-density using the inclined-via based interconnects (namely, via-bonds).

The unique features that differentiate the present invention from the prior arts are: (1) the fabrication method pertains to an elastomeric substrate system; (2) the method is a simple and integrated process in align with the fabrication of multilayer interconnects on PDMS substrates; (3) the density of the achieved bonding is very high; (4) the via-bonds is strong, reliable and resistant to mechanical deformations; (5) the via-bonds occupy a very small area as compared to other bonding methods applied to a PDMS-based system; (6) the via-bonding process is in low temperature (no more than 90°

C.) and CMOS compatible; (7) the process is biocompatible and the resulting microelectrode array systems are suitable for implantation.

These advantages and features of the microfabrication techniques and the resulting SMCM systems of the invention will become more readily apparent from the following detailed description when taken in conjunction with the accompany drawings.

BRIEF DESCRIPTION OF THE SEVERAL VIEWS OF THE DRAWING

The invention is described with reference to the several figures of the drawing, in which, FIG. 1A is a cross-sectional view of a single layer via-bonding process; and FIG. 1B is a cross-sectional view of the SU-8 lift-off method for patterning ultrahigh density interconnects on individual PDMS layers; FIG. 4A is a cross-sectional view of an SMCM enabled by the current invention; and FIG. 4B is a cross-sectional view of another SMCM enabled by the current invention.

DETAILED DESCRIPTION OF THE INVENTION

Figure 2A:
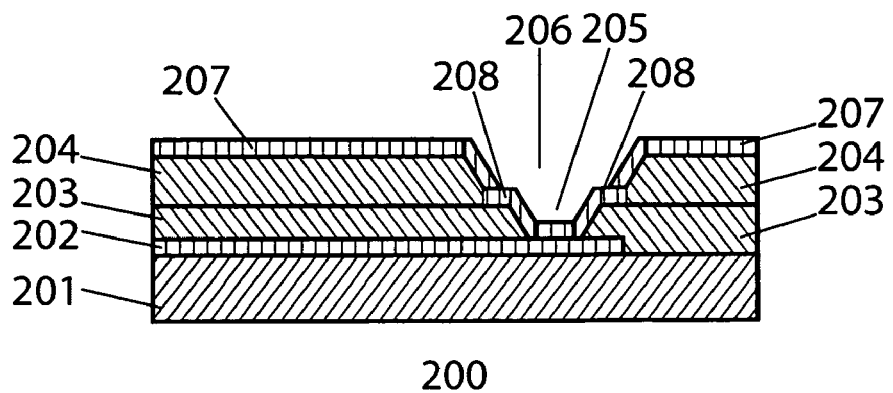
FIG. 2A is a cross-sectional view of a stacked via-bond across two PDMS layers.

At present, PDMS is the softest material that has been used as the fabrication substrate. While its low Young's modulus makes it advantageous in applications where large mechanical deformation of the device is necessary, where an intimate contact to a curved surface is needed, and where mechanical impedance matching to the surrounding soft tissues is desired, however, its low Young's modulus, high coefficient of thermal expansion (more than 100 times than that of silicon), poor adhesion to other microfabrication materials, and porous bulk structure, make the electronic fabrication using PDMS as the substrate extremely challenging, particularly when a high-density electronic system is desired. Most conventional microfabrication techniques that work favorably with other substrate materials, including silicon and other polymers, fail to work when transferred to PDMS-based fabrication. As a result, the integration density and capacity of PDMS-based electronic systems have been low in the prior arts. The invention disclosed herein addresses these fabrication challenges and pushing the integration density and capacity of PDMS-based SMCMs toward a high end to meet the demands of various applications, such as high-resolution retinal prostheses. The invention was developed specifically for PDMS-based microfabrication, but may also have applicability to other substrate material systems.

As the preferred embodiments, the invention herein describes the high-density bonding and interconnection method for the integration of various electronic components into an SMCM structure. Now referring to the drawings and to the following detailed description, detailed information about the invention is provided including the description of specific embodiments. The detailed description serves to explain the principles of the invention. However, the invention is not limited to the particular forms disclosed. The invention covers all modifications, equivalents, and alternatives falling within the spirit and scope of the invention as defined by the claims.

Referring now to FIG. 1, FIG. 1A, generally designated as 100, is the key process for forming the inclined-via based interconnect, herein named as a via-bond, and accordingly the process 100 is called the via-bonding process hereafter. 100 includes five major steps, designated as 101 through 105. The via-bonding process 100 starts with a prepared sample including 106, 107, and 110 in 101. 106 refers to the substrate or electronic component to be bonded and wired. 107 is a bonding pad on the substrate 106. 110 is a thick negative photoresist layer to be patterned using UV lithography. 109 is a purposely added gap between the 110 surface and a photomask 108b. 109 is greater than 500 microns. 108a refers to the collimated incident UV light for transferring the pattern 108c on 108b to 110, in this case 108c is a micro hole.

In 102, after the UV lithography in 101 and a solution development process, the non-exposed part of 110 is removed, leaving a tapered post 111 on top of the bonding pad 107. The novelty of the present invention in 101 and 102 is to add 109 in 101 to modulate the UV light intensity profile passing through 108c by aperture diffraction, so that the exposure results in a tapered post 111. Without 109, that is, 108b directly contacts 110, 111 would have a straight profile. Such a straight profile should be avoided as the purpose is to make an inclined via, because as interconnect, straight vias fail to work with thin film metallization processes in PDMS-based electronic fabrication.

Next in 103, 111 is used to mold an inclined-via in a spin-coated PDMS insulation layer 112. After curing 112 and removal of 111 in acetone, an inclined-via 113 is formed through 112 and exposes the underlying 107 for electrical interconnection as shown in 104. A description of molding microholes through a PDMS layer is shown in U.S. Pat. No. 7,146,221 B2, incorporated herein by reference. And U.S. Pat. App. Pub. No. 2006/0042830 A1 has mentioned to fill the microhole with conductive ink or by electroplating for making interlayer interconnection, incorporated herein by reference. To achieve a much higher wiring density, we use thin film metallization combined with inclined-vias. Our invention, however, is to use the special method in 101 to produce the tapered post 111 for the molding of the inclined-via 113. In 105, the inclined-via 113 is combined with a high-density thin film metallization process to form the via-bond 115 on 107. Conductive films 115 deposited on the slopes and bottom of the inclined-via 113 bridge the interconnect 114 on the top surface with the bonding pad 107 on the substrate 106. The via-bond can be used both to make electrical interconnections between layers of PDMS and, representing one of our major innovations in this invention, to bond the PDMS-based interconnects on another substrate or electronic component. By doing this, we achieved ultrahigh density bondings for interconnection of electronic components embedded in a PDMS substrate. Thus this invention will significantly benefit applications that require high-density wiring, e.g., a 3 $cm^2$ high-resolution retinal electrode array of 600 or more electrodes (methods in prior arts are incapable of achieving this object).

Returning back to 105, the second interconnect layer 114 and 115 is deposited using thin film metallization and patterned using photolithography. The reason for the selection of thin film metallization and photolithography instead of microfluidic channel patterning and stamping as used in U.S. Pat. App. Pub. No. 2006/0042830 A1, is that thin film metallization and photolithography can produce interconnects of much higher density. However, using conventional thin film metallization and photolithography methods as widely used with other substrate materials, it is still impossible to achieve the comparable interconnect density, e.g. a pitch of 20 microns, as that can be achieved on a stiffer substrate, e.g. parylene, polyimide, or silicon. So, we further developed a unique SU-8 lift-off method, generally designated as 120 in FIG. 1B, to be incorporated in 105 to produce ultrahigh density interconnects on individual PDMS layers. A pitch of 20 microns is achieved on PDMS, representing more than one order of magnitude improvement on interconnect density than the prior arts. The combination of 100 and 120 can approach to the wiring and packaging need for, e.g., a high-resolution retinal prosthesis.

Now referring to FIG. 1B for the new SU-8 lift-off method 120. 120 includes three main steps: 121 through 123. In 121, 124 here specifically represents a PDMS substrate, but can be other substrate materials in other processes, as well. 125a is a UV lithographically patterned SU-8 layer, serving as the mask for patterning the interconnects. 126 refers to a spin-coated thin layer of water soluble polymer used as a sacrificial layer for assisting in releasing the SU-8 mask in the end. Without a sacrificial layer in between, the separate of 125a and 126 is impossible without damaging the sample. The water soluble polymer coated in the exposed area 125b is removed by a brief plasma treatment. In 122, 127a and 127b is an anisotropically deposited conductive thin film. Note, no conductive film is deposited on the vertical walls of 125b, as an anisotropic metallization process is required by a lift-off method in general. 127a is directly deposited on the substrate 124. In 123, the sample is soaked in de-ionized water to dissolve 126 from the edges of 127a, and subsequently 125a, together with 127b are lifted off, leaving 127a on the clear 124 as shown in 123.

SU-8 is known for its capability of producing high-resolution, high-density and high-aspect ratio structures. In addition, the use of SU-8 as the photoresist mask together with a water soluble polymer sacrificial layer in 120 provides good adhesion to the underlying PDMS substrate, and the coefficient of thermal expansion of SU-8 is close to that of PDMS, thus avoiding film cracking during cooling down, which is common for other photoresists when applied on PDMS. Therefore, this invented technique can produce an interconnect pitch of 20 microns on PDMS, representing more than one order of magnitude improvement on interconnect density than the prior arts.

With the key method of this invention described above, we now present embodiments that are enabled by this method. By iteration of 101 through 105 in 100 on the same sample, multiple inclined-via based interconnect layers can be produced to significantly boost the wiring capability. Because the via-bonding process 100 is a parallel process, all of the via-bonds through a PDMS layer are formed in a single cycle. In the case that a via-bond need to go through more than one insulation layers, a combination of multiple inclined-vias, each formed in a separate via-bonding cycle, are needed. Using a two-layer example, FIGS. 2A through 2C present three typical structures for using inclined-via based interconnection through more than one insulation layers.

Referring to FIG. 2A, the whole structure is designated as 200 and stacked inclined-vias are used. 201 is the bonding substrate or electronic component with 202 as the bonding pad. An inclined-via 205 is formed on top of 202 in the PDMS layer 203 in the first via-bonding cycle. This via-bonding cycle forms other via-bonds on the bonding substrate (not shown), but leaves the inclined-via 205 free of metal deposition. Then, a second via-bonding cycle is performed with the PDMS insulation layer 204. A larger inclined-via 206 is formed on top of 205 and metal film is deposited in this second cycle to coat the slopes of both 205 and 206. The top interconnect 207 goes down the slopes of 206 and 205 to form a stacked via-bond on 202. Horizontal transitions 208 are allowed since the metallization process coats metal film continuously both on the slopes and horizontal surfaces.

Figure 2B:
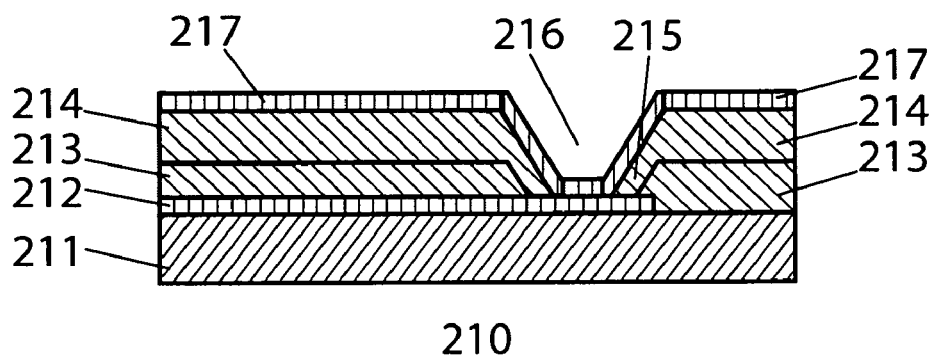
FIG. 2B is a cross-sectional view of another stacked via-bond across two PDMS layers.
Figure 2C:
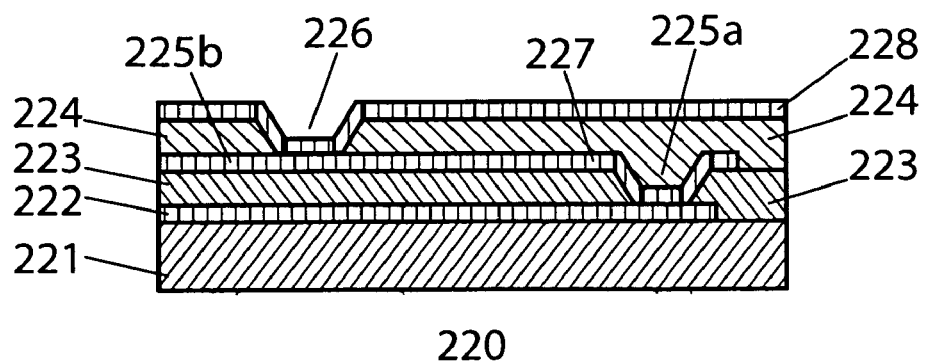
FIG. 2C is a cross-sectional view of relayed via-bonds across two PDMS layers.

Referring to FIG. 2B, the whole structure is designated as 210 and stacked inclined-vias are used. 211 is the bonding substrate or electronic component with 212 as the bonding pad. An inclined-via 215 is formed on top of 212 in the PDMS layer 213 in the first via-bonding cycle. This via-bonding cycle forms other via-bonds on the bonding substrate (not shown), but leaves the inclined-via 215 free of metal deposition. Then, a smaller but deeper via-bond 216 is formed inside of 215 to bond to 212 in a second via-bonding cycle with the PDMS insulation layer 214. PDMS from 214 fills the gaps between 216 and 215. The top interconnect 217 goes down the slopes of 216 to form a deep via-bond on 212.

It is noted that the inclined-vias 205 and 215 can also be coated with metal in the first via-bonding cycle. This is a choice of the design.

Referring to FIG. 2C, the whole structure is designated as 220 and relayed inclined-vias are used. 221 is the bonding substrate or electronic component with 222 as the bonding pad. A via-bond 225a, together with an interconnect 225b, is formed on top of 222 in the PDMS layer 223 in the first via-bonding cycle. Then, another via-bond 216 is formed on top of the interconnect 225b in a second via-bonding cycle with the PDMS insulation layer 224. PDMS from 224 fills the inclined-via 225. The top interconnect 228 is relayed through 226, 225b and 225a to 222.

Figure 3A:
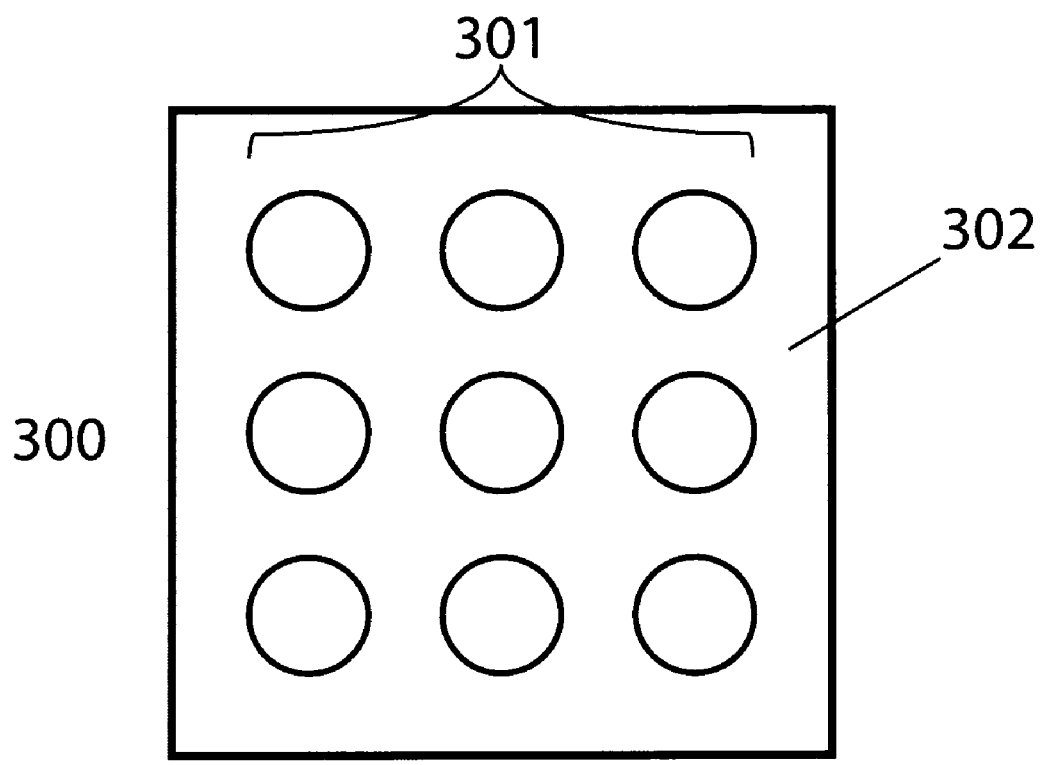
FIG. 3A is a top view an electronic component with bonding pads arranged in an area array.
Figure 3B:
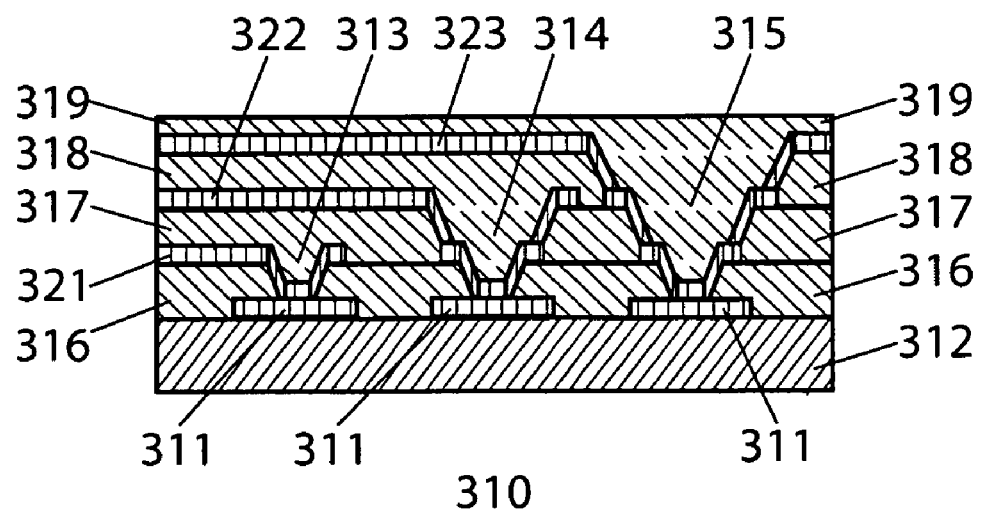
FIG. 3B is the cross-sectional view of the same electronic component bonded and wired using multilayer interconnects.

The high-density bonding capability of the invention is embodied by area array bonding pads and the inclined-via based multilayer wiring. A bonding substrate or electronic component 300 with bonding pads arranged in an area array 301 on the component body 302 is shown as the top view in FIG. 3A. FIG. 3B shows a cross-sectional view 310 of 300 where the bonding pads 311 are bonded and wired using three layers of interconnects 321, 322, and 323. 312 is the component body. 313 is a single-layer via-bond; 314 is a stacked two-layer via-bond; and 315 is a stacked three-layer via-bond. 316 through 319 are difference PDMS layers formed in sequential via-bonding cycles. These PDMS layers are coherently bonded together.

With the basic via-bonding principles defined above, we now give embodiments for the application of this invention to the integrated bonding and interconnection of various thin electronic components to form SMCMs. FIGS. 4A and 4B illustrate two SMCMs. Various components—including printed circuit boards (PCBs), prefabricated silicon integrated circuits (ICs), and thin film discrete components, etc.—embedded on multiple component layers can be connected electrically through multilayer via-bonds to achieve a module-level circuit. The components can be stamped or printed on respective component layers. In FIG. 4A, components are embedded and interconnected in PDMS to form stacked 3-D islands. This architecture can maximize the system-level stretchability. In FIG. 4B, embedded components are not stacked, resulting in decreased stretchability but increased design flexibility as a result of easier wire routing. The resulting SMCMs 400 and 410 can interface with external circuits through exposed connections on the embedded PCBs 401 and 411. Such SMCMs may be rolled into a scroll or folded and thus forming a more compact 3-D circuit. Such SMCMs can withstand mechanical deformation because the deformation is taken up largely by the exposed polymer substrate between the islands. Because cured PDMS bonds to most rigid materials strongly (the bonding can be improved or strengthened by brief oxygen plasma treatment of the rigid substrate before applying PDMS coating), via-bonds on the rigid components are expected to be strong enough to withstand a significantly large amount of strain, and thus should not be the locations for causing mechanical failure during deformation.

Figure 5:
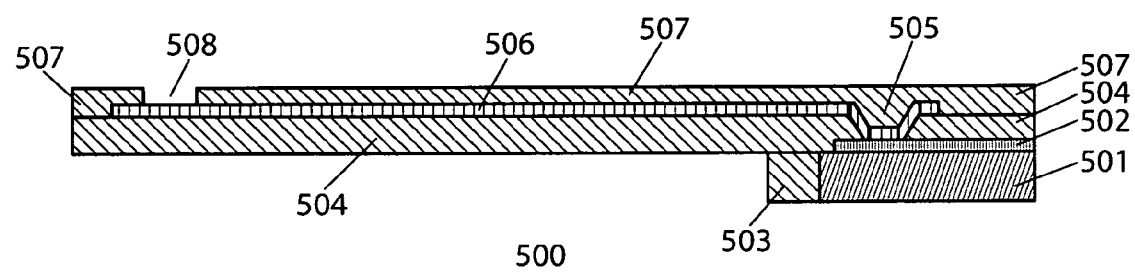
FIG. 5 is a cross-sectional view of a PDMS-based microelectrode array wired to and packaged with another electronic component.

Now referring to FIG. 5, an integrated multielectrode array is shown, and generally designated as 500. A PDMS cable, comprising interconnects 506 sandwiched between two PDMS layers 504 and 507 as described in U.S. Pat. App. Pub. No. 2006/0042830 A1, is used to connect an electrode array 508, as described in U.S. Pat. No. 7,146,221 B2, to an electronic component 501 for external connection, signal amplification or stimulation control. Both U.S. Pat. App. Pub. No. 2006/0042830 A1 and U.S. Pat. No. 7,146,221 B2 are incorporated herein by reference. We incorporate our invention in 500 to provide integrated bonding of the PDMS cable, comprising 504, 506, and 507, to the electronic component 501. Our invention, multilayer via-bonding process, described herein can produce the PDMS-based microelectrode array and the multilayer PDMS cable in the same process as the via-bonding process, so that our invention provides the integrated fabrication, wiring and packaging of high-density microelectrode arrays to form a compact neural implant. Returning to FIG. 5, 504, 506, 507, and 508 are produced in the same process as that produces the via-bond 505 on the bonding pad 502 of 501. PDMS layer 507 is used to encapsulate the whole system. Initially during fabrication, 501 is embedded in a PDMS layer 503. The original 503 extends to the edge of 504. An anti-adhesion layer of Ti/Au thin film is coated on the top surface of 503. After fabrication, 504 and 503 are separated, and extra 503 is cut off, leaving what is shown in FIG. 5.

In FIG. 5, for simplicity, only a single-layer PDMS cable is shown, however, it is noted that a multilayer cable in combination with our invention of multilayer via-bonding can be employed, should the device involves a high-density electrode array that cannot be wired and interconnected to other circuit components using only one layer of interconnects. It is also noted that multiple electronic components, such as multiple IC chips, can also be integrated using the present invention in the stretchable electrode array system.

While the invention is described herein with specific embodiments, it should be understood that the invention is not intended to be limited to the particular forms disclosed. Rather, any modifications, equivalents, and alternatives falling within the spirit and scope of the invention is covered as defined by the following claims.

What is claimed is:

1. A method of bonding flexible interconnects to a substrate, comprising the steps of:
   coating the substrate with a layer of negative photoresist;
   photo-lithographically patterning the negative photoresist layer to produce tapered posts on the substrate wherein said photo-lithographically patterning involves purposely adding a gap between said negative photoresist layer surface and a photomask to modulate the UV light intensity profile by aperture diffraction;
   forming a polydimethylsiloxane layer no thicker than the height of said tapered posts on said substrate wherein said polydimethylsiloxane layer is formed by spin-coating and thermal curing;
   forming inclined-vias in said polydimethylsiloxane layer wherein said inclined-vias have inclined slopes and are molded by said tapered posts after removal of said tapered posts by acetone and plasma etching; and
   patterning thin film interconnects on said polydimethylsiloxane layer wherein the portion of said thin film interconnect deposited on slopes and bottom of said inclined-via electrically connects to a bonding pad on said substrate.

2. The method of claim 1, wherein said flexible interconnects comprises at least one polydimethylsiloxane layer with conductive traces on top of said polydimethylsiloxane layer.

3. The method of claim 1, wherein said substrate comprises at least one bonding pad and is selected from the group comprising pre-fabricated integrated circuit chips, glass, quartz, polyimide, Kapton, Kapton printed circuit boards, FR4 printed circuit boards, parylene, polydimethylsiloxane.

4. The method of claim 1, wherein said purposely added gap is greater than 500 microns and is filled by a transparent spacer comprising an air gap, a vacuum gap, a glass, or a polymer film.

5. The method of claim 1, wherein said patterning thin film interconnects uses methods comprising lift-off metallization, wet-etching, or shadow-masking.

6. The method of claim 5, wherein said thin film interconnects are deposited using processes comprising e-beam evaporation, sputtering, physical vapor deposition, electroplating, or ion implantation.

7. The method of claim 5, wherein said thin film interconnects comprise conductive materials selected from the group comprising of gold, platinum, titanium, platinum and iridium oxide, grapheme, graphite, polypyrrole, poly(3,4-ethylenedioxythiophene).

8. The method of claim 1, further comprising:
   forming a second polydimethylsiloxane layer on said first polydimethylsiloxane layer wherein said second polydimethylsiloxane layer comprises at least one inclined-via; and
   patterning thin film interconnects on said second polydimethylsiloxane layer to form interconnections to conductive interconnects on said first polydimethylsiloxane layer or said substrate through said inclined-vias.

9. The method of claim 8, further comprising:
   forming a third polydimethylsiloxane layer on said second polydimethylsiloxane layer wherein said third polydimethylsiloxane layer comprises at least one inclined-via; and
   patterning thin film interconnects on said third polydimethylsiloxane layer to form interconnections to conductive interconnects on said second or said first polydimethylsiloxane layer or said substrate through said inclined-vias.

10. The method of claim 9, wherein said inclined-vias comprising inclined-vias through a single said polydimethylsiloxane layer, inclined-vias stacked vertically going through multiple said polydimethylsiloxane layers, and inclined-via based interconnections relayed going through multiple said polydimethylsiloxane layers.

11. A lift-off method comprising the steps of:
   forming a sacrificial layer on a substrate;
   forming a layer of SU-8 on said sacrificial layer, wherein said SU-8 layer is patterned by a lithography method comprising UV lithography or e-beam lithography;

removing said sacrificial layer on exposed said substrate in SU-8 windows;

depositing a conductive thin film onto exposed areas of said substrate; and dissolving said sacrificial layer underneath said SU-8 mask to remove said SU-8 mask and excess metal film on top of said SU-8 mask.

12. The method of claim 11, wherein said sacrificial layer comprises water soluble polymers or photoresists.

13. The method of claim 11, wherein said substrate comprises polydimethylsiloxane.

14. The method of claim 11, wherein said conductive thin film comprise materials selected from the group consisting of gold, platinum, chromium, titanium, aluminum, platinum, iridium oxide, graphite, and conducting polymers.

* * * * *